US008858933B2

United States Patent
Alessandri et al.

(10) Patent No.: US 8,858,933 B2
(45) Date of Patent: Oct. 14, 2014

(54) **NEMATICIDAL COMPOSITION COMPRISING *BACILLUS SUBTILIS* AND *BACILLUS LICHENIFORMIS***

(75) Inventors: Abilio Alessandri, Sao Paulo (BR); Inge Knap, Broenshoej (DK); Luciana Sekito De Freitas Zambelli, Sao Paulo (BR)

(73) Assignee: Chr. Hansen A/S, Hoersholm (DK)

( * ) Notice: Subject to any disclaimer, the term of this patent is extended or adjusted under 35 U.S.C. 154(b) by 0 days.

(21) Appl. No.: 13/816,162

(22) PCT Filed: Aug. 9, 2011

(86) PCT No.: PCT/EP2011/063685
§ 371 (c)(1),
(2), (4) Date: Feb. 8, 2013

(87) PCT Pub. No.: WO2012/020014
PCT Pub. Date: Feb. 16, 2012

(65) Prior Publication Data
US 2013/0195826 A1 Aug. 1, 2013

(30) Foreign Application Priority Data
Aug. 10, 2010 (EP) ..................................... 10172373

(51) Int. Cl.
*A01N 63/02* (2006.01)
*C12N 1/20* (2006.01)
*C12R 1/125* (2006.01)
*C12R 1/10* (2006.01)
*A01N 63/00* (2006.01)

(52) U.S. Cl.
CPC ............... *A01N 63/00* (2013.01); *C12R 1/125* (2013.01); *C12R 1/10* (2013.01); *C12N 1/20* (2013.01)
USPC .................. 424/93.7; 424/93.46; 424/93.462; 424/405

(58) Field of Classification Search
None
See application file for complete search history.

(56) References Cited

FOREIGN PATENT DOCUMENTS

| BR | PI0604602-9 A | * | 5/2008 | ............. A01N 63/00 |
| EP | 0705807 A1 | * | 4/1996 | ............. C05F 11/08 |
| WO | WO 2009007192 A1 | * | 1/2009 | ............... C12N 1/20 |

OTHER PUBLICATIONS

Knap, I., B. Lund et al. 2010. *Bacillus licheniformis* prevents necrotic enteritis in broiler chickens. Avian Diseases 54: 931-935. specif. p. 931.*
Siddiqui, Z.A. et al. 1999. Role of bacteria in the management of plant parasitic nematodes: A review. Bioresource Technology 69:167-179. specif. pp. 167, 173-174.*
English (Machine) Translation of BR PI0604602-9 A. 2008. Use of the genera *Bacillus subtilis* and *Bacillus licheniformis* to control phytonematodes in soil. pp. 1-6. specif. pp. 4-6.*
Wikipedia. Habitat. Datasheet [online]. Wikipedia (Page last modified on May 7, 2014). Wikimedia Foundation, Inc. [retrieved on May 7, 2014]. Retrieved from the Internet: <URL: http://en.wikipedia.org/wiki/Habitat> p. 1.*
Wikipedia. Maltodextrin. Datasheet [online]. Wikipedia (Page last modified on Apr. 28, 2014). Wikimedia Foundation, Inc. [retrieved on May 7, 2014]. Retrieved from the Internet: <URL: http://en.wikipedia.org/wiki/Maltodextrin> p. 1.*
Wikipedia. Silicon dioxide. Datasheet [online]. Wikipedia (Page last modified on Apr. 27, 2014). Wikimedia Foundation, Inc. [retrieved on May 7, 2014]. Retrieved from the Internet: <URL: http://en.wikipedia.org/wiki/Silicon_dioxide> pp. 1-2.*

* cited by examiner

*Primary Examiner* — John S Brusca
*Assistant Examiner* — Sharon M Papciak
(74) *Attorney, Agent, or Firm* — Foley & Lardner LLP

(57) ABSTRACT

The present invention refers to a composition comprising *Bacillus subtilis* (DSM 17231) and *Bacillus licheniformis* (DSM 17236) with nematicidal effect against phytonematodes on plants and/or its habitat, to its use and process for its preparation, use of *Bacillus subtilis* (DSM 17231) and *Bacillus licheniformis* (DSM 17236), processes for controlling, combating and conferring specific resistance to phytonematodes, and a kit.

11 Claims, 4 Drawing Sheets

NEMATICIDAL COMPOSITION COMPRISING *BACILLUS SUBTILIS* AND *BACILLUS LICHENIFORMIS*

CROSS-REFERENCE TO RELATED APPLICATIONS

This application is a national phase of PCT/EP2011/063685, filed Aug. 9, 2011, which was published on Feb. 16, 2012, as WO 2012/020014 A1, which claims the benefit of EP 10172373.2, filed Aug. 10, 2010. The respective contents of these documents are incorporated here by reference in their entirety.

SUMMARY OF THE INVENTION

The present invention relates to a composition comprising *Bacillus subtilis* and *Bacillus licheniformis* with nematicidal effect against phytonematodes on plants and/or its habitat, to its use, to a process for its preparation, to the use of *Bacillus subtilis* and *Bacillus licheniformis*, to processes for controlling, combating and/or conferring specific resistance to phytonematodes, and to a kit. Particularly, the invention relates to *Bacillus subtilis* (DSM 17231) and *Bacillus licheniformis* (DSM 17236).

FIELD OF THE INVENTION

Intensification of agricultural activity has caused an ecological imbalance, making it necessary for use of selective products that do not affect the balance between pests and their predators, parasitoids and pathogens, responsible for much of the natural biological control, since they retain pest population levels acceptable (DENT, D., Insect pest management. Cambridge: Cabi Bioscience 2000).

In order to reverse this situation, it is recommended to develop programs for integrated pest management, defined as a decision system for the use of control tactics, singly or combined harmoniously in a management strategy based on cost/benefit that take into account the interest and/or impact on farmers, society and environment. Among the control measures available for these management systems are entomopathogenic nematodes and insect parasitoids, which cover different areas of biological pest control.

In the current context of a modern and ecologic society, which is concerned with preserving the environment, biological control is considered an attractive alternative and/or supplement to conventional methods of control. Biological control is the use of one organism (predator, parasite or pathogen) that attacks another organism which is causing economic damage to crops. This is a very common strategy in agro ecological systems, as well as in conventional agriculture which relies on the Integrated Pest Management (IPM).

Although the biological control brings positive responses in the reduction or withdrawal of pesticide use and improving farmers' income, the analysis of the set of experiments worldwide, shows that the results are still concentrated in only a few crops. There is still much to develop in areas of control of pests and diseases.

There has been a great emphasis on research on biological control with the use of bacteria colonizing the roots of plants, called rhizobacteria. The beneficial rhizobacteria for promoting growth and/or acting in the biological control of plant pathogenic bacteria are called plant growth-promoting rhizobacteria or PGPR. The PGPR increases the availability of nutrients to the plant and can produce combinations and concentrations of substances that promote growth. However, the major effect of these rhizobacteria is to suppress plant pathogens deleterious to the growth of these plants. Inhibition of these harmful bacteria is through the production of siderophores, substances that act under conditions of low phosphorus availability by further reducing the phosphorus available to other rhizosphere microorganisms or the production of antibiotics.

STATE OF THE ART

The pressure of society to replace the nematicides with environmental acceptable products or ecological techniques has encouraged the search for alternative methods to control nematodes. In this context, biological control has been considered one of the alternatives within an integrated approach, in which one seeks to ensure sustainable development of agriculture. The use of natural enemies has become a field of research, which may act to reduce nematode populations below the threshold level of economic damage.

The risks to humans and environments presented by using synthetic pesticides emphasize the need for tools such as biological control in optimizing sustainable agricultural systems.

European patent application EP 0705807A1 relates to a bacterial preparation for soil conditioning which comprises bacteria belonging to genus *Bacillus*, such as *Bacillus subtilis* and *Bacillus licheniformis*. The preparation can prevent the injuries to roots of crops caused by nematodes.

Brazilian patent application BR PI 0604602-9A relates to use of a *Bacillus subtilis* in conjunction with *Bacillus licheniformes* for control of phytonematodes.

Siddiqui and Mahmood (1999) describe the role of bacteria in the management of plant parasitic nematodes showing that *Bacillus subtilis* and *Bacillus licheniformis* can be useful against phytonematodes, such as *Meloidogyne* spp., *Heterodera* spp. and *Rotylenchulus*.

The inventors of the present invention have proceeded with extensive screening and research in order to solve the object of providing biological methods of controlling nematodes based on the identification of two wild-type *Bacillus subtilis* and *Bacillus licheniformis* strains, which are particularly capable of reducing injuries to roots of crops caused by nematodes.

DETAILED DESCRIPTION OF THE INVENTION

Rhizobacteria

Figure 1:
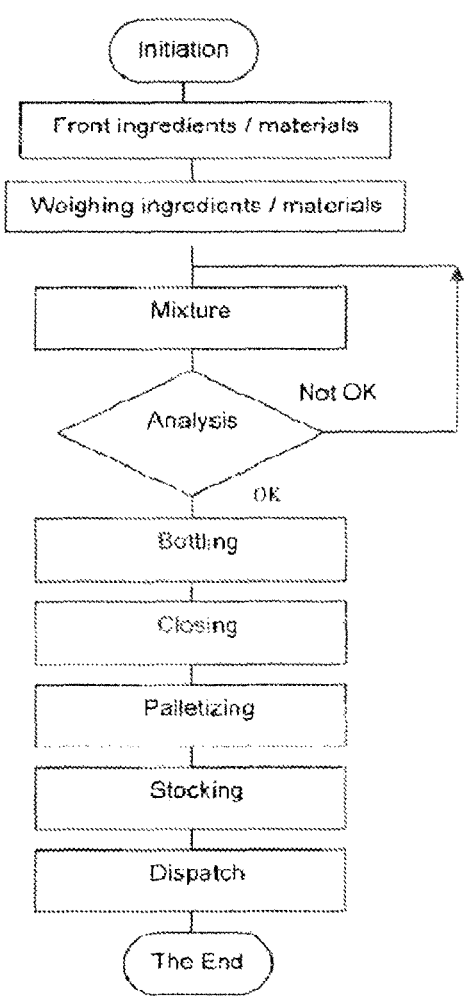
FIG. 1—Flow of the operating conditions of the manufacturing processes of mixing.

The soils are home to a complex biological community, of which microorganisms, prokaryotes and eukaryotes form a majority, both in number and in diversity. Some prokaryotes have ecological niches as the rhizosphere, and/or the rhizoplane of plants, where they multiply, survive and protect themselves from the rest of the antagonistic action of soil microflora. These organisms have been generically called rhizobacteria.

In association with plants, rhizobacteria may have a deleterious effect, null or beneficial. Those who exercise a beneficial effect—growth promotion and biological control of disease—are called PGPR ("Plant Growth-Promoting Rhizobacteria). It is estimated that only 0.6% of rhizobacteria have some beneficial effect for the plant with which they are associated.

PGPR as Biocontrol Agents

PGPR have been used for biological control of plant diseases and thereby increase the productivity of crops. How and why this biological control is exercised, is still a topic that needs complementary studies.

In some situations, it is possible that biological control occurs by direct antagonism exerted by PGPR against the pathogen, with involvement of the known mechanisms of antibiosis: production of antimicrobial substances, direct parasitism, competition for nutrients and ecological niches. Research has shown that certain PGPR appear to act as elicitor of ISR (induced systemic resistance), in the sense that the plant becomes systemically protected against more than one pathogen, unlike the classical biological control, which aims to implement the control more specifically.

When PGPR colonize the root system, the constituent molecules of the bacterial cell or synthesized by it act as elicitors of a biochemical signal. This signal is translocated to sites distant from the site of its origin. Genes coding for the synthesis of components of the dynamic resistance are disabled and expressed in the induced systemic resistance.

Some rhizobacteria produce toxic metabolites that affect the movement of nematodes in vitro, while others inhibit the hatching of juveniles and the process by which they penetrate to the roots.

Effect of Rhizobacteria on Plant Parasitic Nematodes

The control that the rhizobacteria exert on nematodes can be implemented in various ways and may effect different phases of the nematode life cycle:

Egg: antibiotics and toxins produced by bacteria in the rhizosphere diffuse into the soil and can be absorbed by the eggs of the nematodes, killing cells and preventing their embryonic development.

Hatching: rhizobacteria degrade the root exudates that act as hatching factor for many species of nematodes and then there is the possibility that compounds absorbed by the nematode egg inactivate or cause deformation during development that prevent hatch.

Targeting and mobility: The transformation of root exudates in the metabolic byproducts of rhizobacteria can cause the nematode simply to not recognize the chemotropic stimulus, so it would continue to move randomly, and eventually to deplete its energy reserves and die without entering the root. If the nematode recognizes the root exudates and moves towards the roots, some bacterial products can present nematostatic characteristics and reduce the mobility of the nematode to impede it reaching the root.

Recognition of the host: Substances produced by rhizobacteria are absorbed by roots and can alter their chemical composition, causing the nematodes not to recognize their host. It is also believed that the rhizobacteria bind to lectins on the surface of roots, characterized by being the binding site between the nematode and its plant host, thereby preventing recognition.

Penetration in the root: toxin or repellant produced by rhizobacteria in high concentration in the region of the rhizoplane or in the cellular content of the epidermis of roots, can discourage the penetration of nematodes in the host plant.

Food: the rhizobacteria, or their metabolic products, can be absorbed by the plant and the latter to perceive the presence of the nematode, trigger a hypersensitive reaction in giant cells, which is the main mechanism of host resistance to nematodes of the genus *Meloidogyne*. This resistance, called systemic resistance, is not intrinsic to the plant, that is, a reaction that is induced in it by the presence of PGPR.

Reproduction: Some rhizobacteria have a greater effect on the reduction of eggs than in reducing the number of galls, this may be one of the operating mechanisms.

The Rhizosphere Environment

One of the most convenient methods of introducing a rhizobacteria in the root environment is through the application on the seeds before sowing. The process of seed germination releases carbohydrates and amino acids in abundance in the form of seed exudates. Thus, these organisms introduced with the seeds in the soil utilize exudates as a source of nutrition and colonize the roots as they emerge. Rhizobacteria isolates that have greater ability to utilize root exudates of seeds may have selective advantage in colonization of roots.

Rhizobacteria of the genus *Bacillus* have been associated with nematode control. Sikora, R. A. (Interrelationship between plant health promoting rhizobacteria, plant parasitic nematodes and soil microorganisms. Medicine Faculty Landbouww Rijksuniv Gent, Landbouww, v.53, n.2b, p. 867-878, 1988) observed reductions in infection of *Meloidogyne arenaria, M. incognita* and *Rotylenchulus reniformis* around 60-65% with treatment of seeds of various crops with a strain of *Bacillus*.

Advantages of Rhizobacteria for Commercial Application

The rhizobacteria have a number of advantages over nematicides or even on other biological control agents: they are easy to mass-produce, they are easy to store, they are adaptable to the formulation technology and require no genetic manipulation.

The rhizobacteria can be applied by treating the substrate, immersing the seedling root systems in bacterial suspensions, watering the plant with bacterial suspension by dipping the seeds in suspension of rhizobacteria or by applying PGPR with the pelleting of seeds in alginate.

Bacteria of the Genus *Bacillus*

The *Bacillus* species are Gram-positive bacteria characterized by having thick cell walls and the absence of outer membranes, which differs from the Gram-negative bacteria. Much of the walls of Gram-positive bacteria is composed of peptidoglycan.

Gram-positive species are divided into groups according to their morphological and biochemical characteristics. The genus *Bacillus* is belonging to the group of sporulated bacteria. Species with spore-forming structures that are resistant to environmental changes, sustain dry heat and certain chemical disinfectants for moderate periods of time. They persist for years on dry land.

Use of *Bacillus* spp. in the Control of Nematodes

Nematodes are responsible for severe losses in agricultural production. The estimated losses are around $ 100 billion per year worldwide in economically important crops.

The use of cultivars resistant to nematodes is not always possible due to lack of resistance sources for breeding, lack of adaptability of cultivars resistant to certain regions and planting seasons, or the breakdown of resistance in field conditions. Chemical control of nematodes is generally not recommended because it is not very effective; it is expensive, because the waste it leaves in food and the environmental contamination it causes. Because of these disadvantages, there is an increased pressure from society to restrict the use of chemicals which results in a demand by farmers for products that are at the same time, non-toxic to humans and animals, cheap and very effectively control nematodes.

Many soil microorganisms are known as parasites or predators of nematodes. The action of these microorganisms can result from direct or indirect effect through interference with steps in the life cycle of the pathogen.

Bacillus subtilis

The beneficial effect of *B. subtilis*, when applied near the seed or the soil, is not solely due to the antagonism afforded to pathogens. The bacterium has a positive influence on germination, development and crop yield due also to the production of substances which promote growth and improvement in plant nutrition by solubilization of phosphorus.

Genus Meloidogyne

Nematodes of the genus *Meloidogyne* (root-knot nematodes) exhibit great diversity on plant hosts and occur in various regions of the globe, causing losses in different cultures. The main symptom is the presence of galls on plant roots. These galls are malformations or thickening of the root system. The affected plants show up weak, have low production, early defoliation and premature decline, and there may occasionally be plant death, with symptoms potentiated under conditions of nutrient stress and drought.

Initially, the second stage juveniles (J2) of *Meloidogyne* penetrate the roots and establish a feeding site in the region of the central cylinder of roots. Through the development of the nematodes, the J2 differentiate into adult males or females. Adult males, leave the root system, and the females remain in the roots. During the development of female *Meloidogyne* approximately 500 eggs are laid. They are deposited in a gelatinous matrix outside the roots of which the J2 hatch, and they thereby re-infect the root system. The life cycle of root-knot nematodes are approximately four weeks and may extend under temperature conditions less favorable. Temperatures below 20° C. or above 35° C. and conditions of drought or water logging of the soil reduces the development and survival of the nematode.

The control of *Meloidogyne incognita* and *M. javanica* can be done with the use of chemicals that contain certain active ingredients such as carbofuran, etoprophos, aldicarb, metham-sodium or fenamiphos, among others, depending of the culture in question. The practice of crop rotation is also important in control due to deployment of non-host crops such as peanuts, pineapple, rice, or use plant species as ground cover also non-host such as oats.

The nematode *Meloidogyne exigua* is very aggressive and is very widespread in the plantations. Different methods of chemical control in areas infested by *M. exigua*, include the use of chemicals that contain any of the active ingredients terbufos or carbofuran, depending on the kind of culture. Among the non-host crops, stand out are cotton, peanuts, rice and oats.

Like *M. exigua*, *M. paranaensis* is widespread in the culture of coffee, but is not much of a problem in other cultures. As for its control, positive results has been obtained by the fungus *Paecilomyces lilacinus*, and this reduced the nematode populations in roots of the tomato "Santa Clara" in the greenhouse.

The use of rhizobacteria in relation to biological control is already known. However, the Applicant presently developed a composition comprising two species of *Bacillus*, namely: *Bacillus subtilis* DSM 17231 (also known as DSM 5750) or a mutant thereof and *Bacillus licheniformis* DSM 17236 (also known as DSM 5749) or a mutant thereof with nematicidal effect against phytonematodes in a plant culture.

Thus, the first aspect of the invention relates to the herein described novel strains or mutants thereof.

It is clear for the skilled person that by using the deposited strains as starting material, the skilled reader can by conventional mutagenesis or re-isolation techniques routinely obtain further mutants or derivatives thereof that retain the herein described relevant features and advantages. Accordingly, the term "a mutant thereof" of the first aspect relates to mutant strains obtained by using the deposited strain as starting material.

Phytonematodes are broadly considered any nematode having a negative impact on commercial crops. Nematodes which can be combated using the composition of the present invention include nematodes of the genus: *Meloidogyne, Pratylenchus, Heterodera, Globodera, Ditylenchus, Tylenchulus, Xiphinema, Radopholus, Rotylenchulus, Helicotylenchus* and *Belonolaimus*. Species of the genus *Meloidogyne* are considered of particular relevance as they are responsible for around 95% of all infestations on crops causing approximately 5% of all crop losses worldwide. The composition of the present invention may, besides the active components, contain agrochemical acceptable excipients and/or vehicles thereof. The composition of the invention further comprises agrochemically acceptable carriers, vehicles and/or adjuvants.

The composition of this invention particularly serves to combat nematodes in crop plants.

Among the main crops of plants are sugar cane, coffee, soybeans, cotton, corn, potatoes, tomatoes, tobacco, banana, rice, wheat, avocado, pineapple, squash, cacao, coconut, oats, onion, lettuce, beet, carrot, cassava, beans, sunflower, pepper, turnip, apple, strawberry, okra, radish and onion.

With regard to fruitculture: citrus, grape, guava, papaya, fig, peach, plum and nespeira are of particular relevance and with regard to horticulture: eggplant and cruciferous.

With regard to floriculture: rose, chrysanthemum, lisianthus, gerbera, amaryllis, begonia and celosia.

The present invention relates to a composition comprising *Bacillus subtilis* DSM 17231, or a mutant thereof, and *Bacillus licheniformis* DSM 17236, or a mutant thereof, and to a kit comprising the composition, or prepared by the process of preparing the composition, as well as instructions and a suitable recipient.

A process for preparing a composition comprising *Bacillus subtilis* DSM 17231, or a mutant thereof, and *Bacillus licheniformis* DSM 17236, or a mutant thereof, together with agrochemically acceptable carriers, vehicles and/or adjuvants, and use of said composition for controlling, combating and/or conferring specific resistance to phytonematodes are also given.

In addition, the invention refers to the use of effective amounts of *Bacillus subtilis* DSM 17231, or a mutant thereof, and *Bacillus licheniformis* DSM 17236, or a mutant thereof, in the manufacture of an agrochemical composition with nematicidal effect against phytonematodes in a plant culture, as well as processes for controlling, combating and/or conferring specific resistance to phytonematodes.

The illustrative examples presented below serve to better describe the present invention. However, the formulations

EXAMPLES

Composition of the Invention

| Ingredients | Percentage min. (%) | Percentage max. (%) |
|---|---|---|
| Bacillus subtilis (DSM 17231) | 2.4 | 3.0 |
| Bacillus licheniformis (DSM 17236) | 2.4 | 3.0 |
| Maltodextrin | 93.0 | 94.2 |
| Silico dioxide | 1.0 | 1.0 |

Bacillus subtilis (DSM 17231): $1.6 \times 10^{10}$ ufc/g
Bacillus licheniformis (DSM 17236): $1.6 \times 10^{10}$ ufc/g The composition can be employed as wettable powder. The composition also be provided in any other suitable form e.g. as a powder, solution, slurry, granules etc.
Operating Conditions of the Manufacturing Processes of Mixing:
Front ingredients/materials: The receipt is carried out by trained personnel for verification and checking of goods received. According to production targets, a list of ingredients and their quantities is issued and the information is sent to the factory.
Weighing ingredients/materials: The ingredients are received at the factory, weighed and placed in a stainless steel mixer.
Mixture: The ingredients are mixed following the treatment described in SOP (Standard Operating Procedure).
Analysis: Samples are collected for counting the number of colonies in CFU/g.
Bottling: The product is packed in bags with internal protection kraft containing 20 kg or polyethylene plastic pots containing 1.0 or 5.0 kg.
Closing: The bags are sealed and stitched. The pots are sealed with cap and passed through magnetic induction.
Palletizing: Still in the factory packaging are placed on wooden pallets awaiting review by the Quality Control (QC).
Stocking: The final product is stored, sealed and properly identified. Each batch is recorded in an electronic program, available to all operators in each sector of interest.
Dispatch: Once released by the QC, the product remains stored in the warehouse of dispatch to the time of sale.
This flow is shown in FIG. 1.
In Vitro Tests:
Test 1
Objective: to evaluate the in vitro effect of biological products based on Bacillus bacteria in the control of phytonematodes, namely, Meloidogyne incognita, M. javanica, and M. paranaensis.
Material and Methods:
We studied three specks of phytonematodes of the genus Meloidogyne: M. incognita, M. javanica, M. paranaensis and two biological products in two different doses: A Japanese product based on a Bacillus species and the product NEMIX® composed of Bacillus subtilis and Bacillus licheniformis 97.8% lactose and silicon dioxide. The nematicide used as a standard of effectiveness was 150G TEMIK® (aldicarb), whose characteristics are:
  Trademark: TEMIK 150
  Registrant: Bayer CropScience Ltda.
  Grade(s): Miticide—insecticide—nematicide
  Formulation: GR—Granular
  Active Ingredient (i.a.) aldicarb
  Concentration of i.a.: 150 g/Kg
  Method of Application: terrestrial
  Mode of Employment: soil
  Toxicological Classification: I—Extremely toxic
The experiment had six treatments
Water: absolute control;
P1D2: Japanese product at a dose of 2 kg.ha$^{-1}$;
P1D4: Japanese product at a dose of 4 kg.ha$^{-1}$;
NEMIX® product at a dose of 2
NEMIX® product at a dose of 4 kg.ha$^{-1}$;
Nematicide aldicarb (TEMIK® 150G) at a dose of 15 kg.ha$^{-1}$.
Nemix product at a dose of 4 kg.ha$^{-1}$;
Nematicide aldicarb (TEMIK® 150G) at a dose of 15 kg.ha$^{-1}$.
Test for Evaluating Products in the Activity of the Nematode:
Obtaining $2^{nd}$ Stage Juveniles of Meloidogyne
Coffee and tomato roots infected by Meloidogyne species were washed to remove excess soil adhered to them, cut and processed by the technique of blender (BONETI, J. I. S. & FERRAZ, S.: Modificação de método de Hussey e Barker para extração de ovos de Meloidogyne exigua de raizes de cafeeiro. Fitopatologia Brasileira, Brasilia, DF, v.6, n.3, 553p, 1981).
The roots were cut into fragments about 1 cm long, were placed in a blender, filled with a solution of sodium hypochlorite 0.5% active chlorine to cover the material. The blender was turned on its lowest speed for 40 seconds on average. Then the suspension obtained was passed through a sieve of 100 mesh superimposed on a 500 mesh. The waste was collected from a 500 mesh sieve with the aid of jets of water from a squeeze for a cup of Becker, carefully so that the final volume to be as concentrated as possible.
The suspensions were centrifuged for 5 min at a speed of 650 gravities. Carefully, the supernatant was discarded and the inner wall of the centrifuge tube was cleaned to remove organic impurities.
To the residue of each tube a sucrose solution (of a concentration of 454 g of sugar to one liter of water) was added, mixed well and the centrifuge was switched on at the same speed for 1 min as described earlier.
The supernatant was poured through a sieve of 500 mesh, washed with water to remove excess sucrose and collected with the aid of jets of water from a piseta in a cup of Becker.
Petri dishes with a diameter of 5 cm were inside a nylon containing layer of facial tissue paper. The suspension of eggs was added over the layer of tissue paper and the Petri dishes were placed in incubator at 30° C. for 24 hours. After 24 h the screen with the tissue was suspended by the aid of forceps and the fluid inside the petri dish was removed to a plate Becker and washed with water. The screen was replaced with a paper plate and water was added. The plates remained in the incubator for 48 h.
After 48 h, the screens were removed and the liquid collected with the aid of jets of water from a piseta for a cup of Becker. The suspension was calibrated to contain 250, 50, 20 and 100 2nd stage juveniles/mL of Meloidogyne incognita, M. javanica, and M. paranaensis for assembly of in vitro test, respectively.
Installation and Evaluation of the in Vitro
Petri dishes with a diameter of 11 cm containing a layer of water-agar 2% received 1 mL, of the suspension of juvenile 2nd stage and 1 mL, of each treatment to be tested: distilled water solution TEMIK® 150G (nematicide); solution of the Japanese product based on *Bacillus* in two strengths; NEMIX® solution of the product in two strengths. With spin, the two were thoroughly mixed mL. The plates were kept in the incubator at 30° C. for 7 days.

After 7 days, each plate was examined under a magnifying glass for verification and counting of nematodes assets.

Testing for Evaluating the Inhibition of Hatching of Juvenile 2 Stage *Meloidogyne*

Roots of tomato and coffee were prepared for the blender (BONETI, J. I. S.; FERRAZ, S.: Modificação de método de Hussey e Barker para extração de ovos de *Meloidogyne exigua* de raizes de cafeeiro. Fitopatologia Brasileira, Brasilia, DF, v.6, n.3, 553p., 1981), previously described in section "Obtaining 2nd stage juveniles of *Meloidogyne*".

The suspensions were calibrated to contain 1500 eggs/mL, 100 eggs/mL, 500 eggs/mL and 200 eggs/mL of *M. incognita*, *M. javanica*, and *M. paranaensis* respectively.

Installation and Evaluation of the in Vitro

Petri dishes with a diameter of 5 cm, containing in its interior, nylon fabric with a layer of tissue paper moistened, received 1 mL of each treatment being tested and 1 mL of the suspension of eggs. The plates were kept in incubator at 30° C. for 7 days.

After 7 days, the screens were removed and the liquid from each plate was collected, using jets of water from a piseta to a glass.

Each suspension was examined under the microscope with the aid of a counting chamber for verification and counting of $J_2$ of *Meloidogyne*.

Design and Statistical Analysis

The experiment was a completely randomized design with six treatments and five replicates for each nematode. Each petri dish was the experimental unit.

The data were subjected to statistical procedures program Sisvar (FERREIRA, D. F.: Análises estatisticas por meio do Sisvar para Windows versão 4.0. In: REUNIÃO ANUAL DA REGIÃO BRASILEIRA DA SOCIEDADE INTERNACIONAL DE BIOMETRIA., 45, 2000, Sao Carlos: UFSCar, 2000, p. 255-258, 2000). In statistical analysis, data were subjected to analysis of variance and means compared by Scott-Knott test at 5% probability. (Results showing no statistically significant difference are marked with identical lower case letters in the figures).

In evaluating the effect of pesticides in controlling nematodes, were calculated percentage inhibition of movement and percentage inhibition of hatching of juveniles. The formula used in calculating these percentages were as follows:

$$\frac{(B-A)}{B} \times 100 \text{ where:}$$

$A$ = number of active nematodes or hatched in each repetition of each treatment $B$ = number of nematodes used in the assay to evaluate inhibition of movement or the inhibition of hatching.

Results and Discussion

Figure 2:
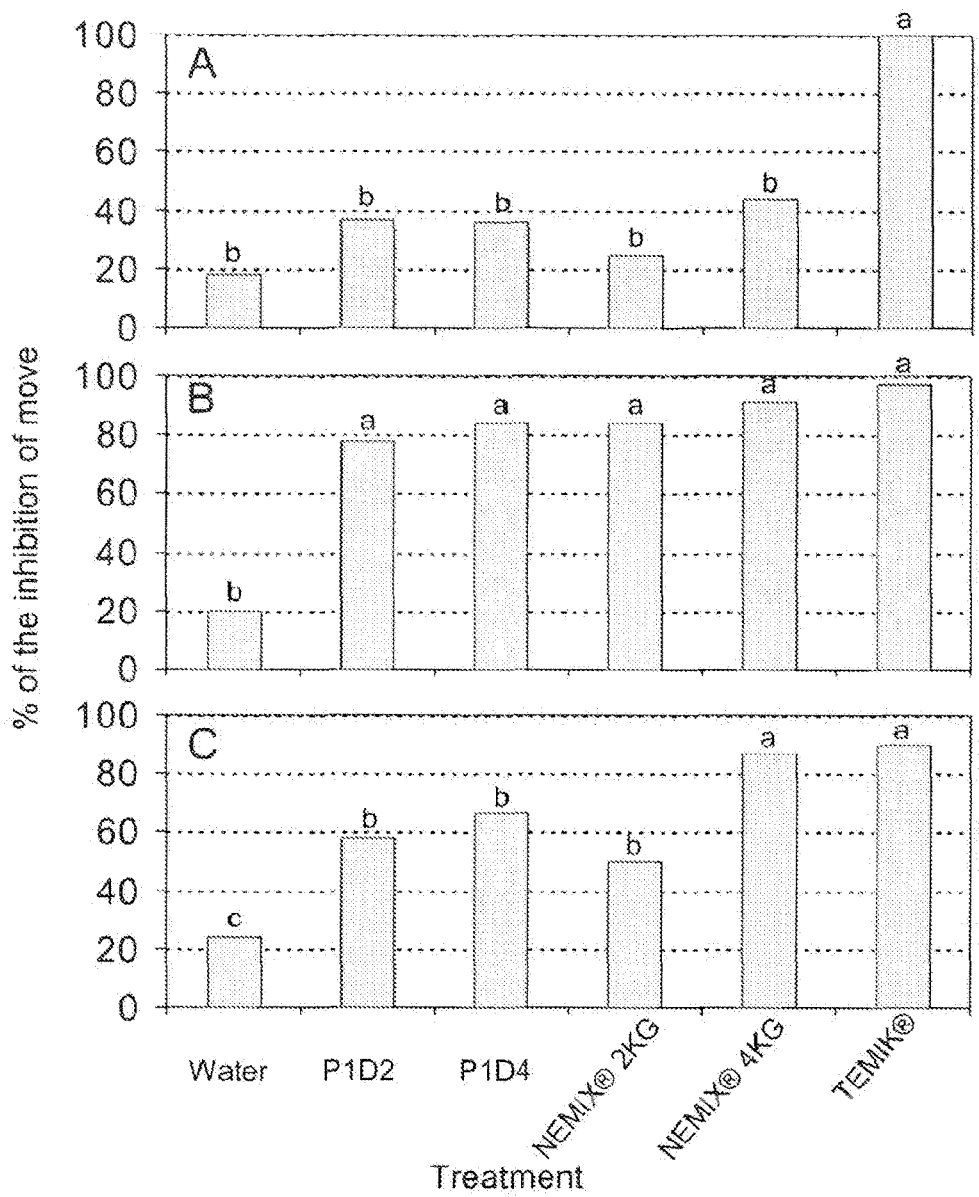
FIG. 2—Percentage of inhibition of movement of juveniles after effect of biological products. A: *Meloidogyne incognita*; B: *M. javanica*, C: *M. paranaensis*.
Figure 3:
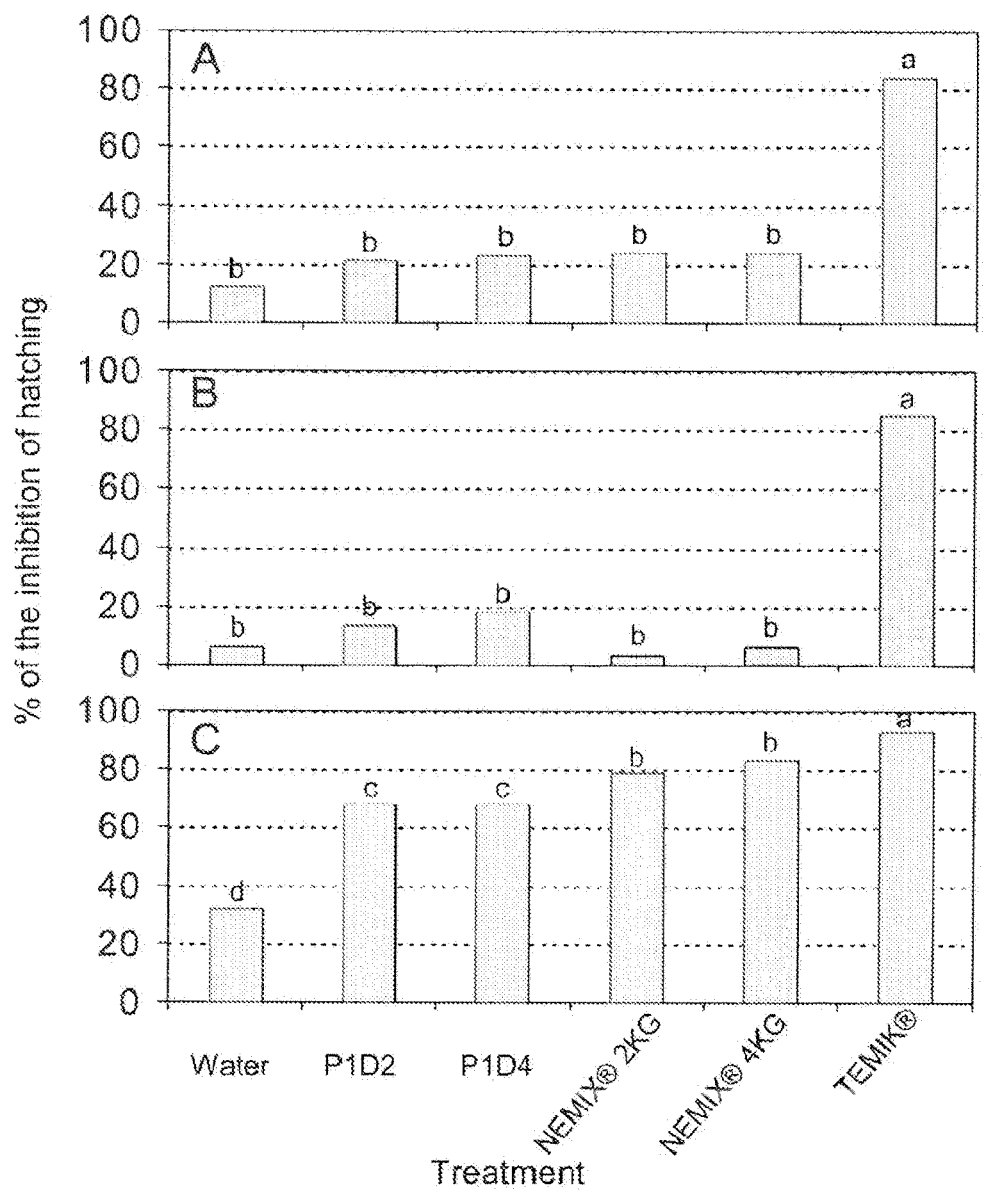
FIG. 3—Percentage of inhibition of hatching after effect of biological products. A: *Meloidogyne incognita*; B: *M. javanica*, C: *M. paranaensis*.
Figure 4:
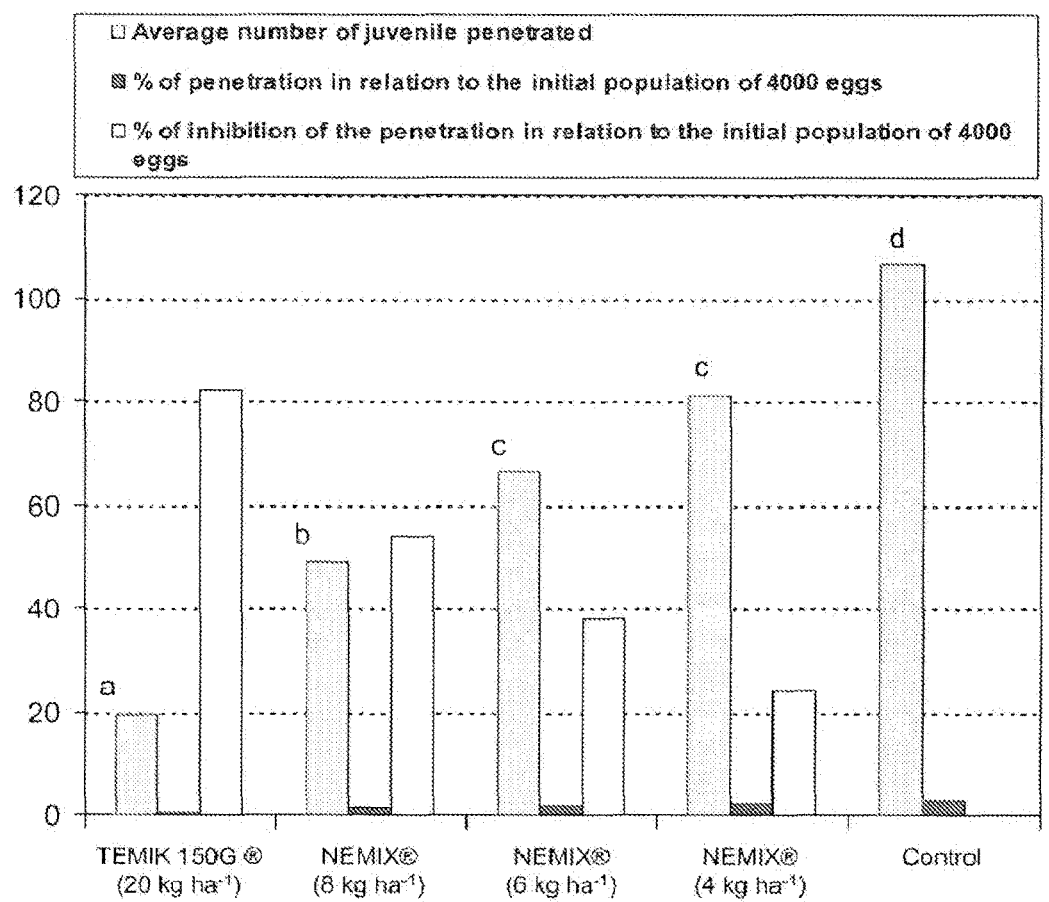
FIG. 4—Average number of second stage juveniles of *Meloidogyne exigua* penetrated, percentages of penetration and inhibition of penetration in roots of tomato. 'Santa Cruz Kada Gigante', three weeks after inoculation.

FIGS. 2 and 3 illustrates the inhibitory effect of different nematocides on movements (FIG. 2) and hatching (FIG. 3) of the nematodes *M. incognita* (A), *M. javanica* (B) and *M. paranaensis* (C).

The data presented in FIG. 2A illustrates that only the nematicide TEMIK® differed significantly from other treatments featuring the best outcome for mortality and inhibition of hatching of juvenile *M. incognita*. Regarding the inhibition of hatching of juveniles, it was observed that the treatments did not differ from the control and only the chemical treatment with TEMIK® reduced hatching.

For the inhibition of *Meloidogyne javanica* no significant difference was observed between the biological products tested and TEMIK®, showing that the biological products had satisfactory effect on the inhibition of motion of the nematode (FIG. 2B). The effect on hatching was not significant and only the chemical product TEMIK inhibited hatching (FIG. 3B).

For the inhibition of *Meloidogyne paranaensis* the NEMIX® dose of 4 kg ha-1 gave a result significantly equal to nematicide (FIG. 2C). Following, are the Japanese products in doses of 2 and 4 kg ha-1 and NEMIX® at a dose of 2 kg ha-1, and all organic products had greater effect than the control treatment. Regarding the inhibition of hatching of juveniles, the product NEMIX® with two doses had similar effects showing the best results among the biological products tested (FIG. 3C). All products tested differed from the absolute control and nematicide effect was superior to all other treatments.

The product TEMIK® and NEMIX® at a dose of 4 kg ha-1 were the most effective and do not differ significantly with respect to mortality of *M. parananensis*. Regarding inhibition of hatching, TEMIK® differed significantly from all other treatments being superior to them. However, the NEMIX® product was more effective than the Japanese product (FIG. 3C).

Thus, the composition NEMIX® showed a significant inhibition of the nematodes *M. javanica* and *M. paranaensis* an inhibition comparable to the chemical product TEMIK®.

Test 2

Objective: to evaluate the penetration of *Meloidogyne javanica* in tomato roots in relation to different doses of the biological product NEMIX® comprising *Bacillus subtilis* and *Bacillus licheniformis* under conditions of greenhouse.

Obtaining the Inoculum

Getting the inoculum was made from the sample processing of coffee roots infected by *M. javanica*. The samples were taken to the Agricultural Nematology Laboratory of Institute of Agricultural Sciences and for processing, the roots were chopped into fragments of 2 cm and placed in a household blender cup containing sodium hypochlorite solution (1 part bleach: 4 parts water).

The solution was spinned for 20 seconds. After this period, the suspension passed through a set of sieves of 200 and 500 mesh, respectively, overlap. The residue from the sieve of 500 mesh was collected, with the aid of a squeeze with water to a beaker. The suspension obtained was calibrated to contain 800 eggs nematóide.mL$^{-1}$.

Installation and Driving Test

The experimental design was completely randomized design with five treatments and five replications.

The tomato cultivar used was 'Santa Cruz Kada Gigante', with the doses used of the biological product NEMIX of 4, 6 and 8 kg ha-1. The nematicide aldicarb (TEMIK® 20 G 150 kg ha-1) was used as a standard check and control without any tomato product and the plant parasitic nematode *M. javanica* for the standard penetration.

The seeds of tomato cultivar 'Santa Cruz Kada Gigante' were sown in styrofoam trays of 128 cells filled with substratum Plantmax®. For inoculation, three holes were opened with 2 cm deep and spaced 2 cm from the stem of the seedling. In these three holes were distributed 5 ml suspension calibrated inoculum (4000 nematode/plastic cup). Soon after, the doses of the products were added in small plastic cups in open pits around each seedling.

Evaluation of the Penetration of Juvenile Second Stage of *M. javanica* in Roots of Tomato The evaluation was done after 3 weeks of inoculation, where the roots after cutting the shoots and the separation of soil, were prepared for staining nematodes in plant tissues (Byrd Jr. et al., An improved technique for clearing and staining plant tissues for detection of nematodes. Journal of Nematology, Lakeland, v. 5, n. 1, p. 142-143, 1983). The roots were fractured into pieces 1-2 cm and transferred to a cup Becker 50 mL of water to which were added 20 mL of commercial bleach (5.25% NaOCl), which resulted in a final concentration of 1.5% NaOCl. The root segments remained for 6 min in this solution, promoting a manual shaking for 10 s at intervals of 1 min. The roots were washed under running water for 30 to 45s and kept at rest for 15s in water to remove residual sodium hypochlorite.

Then, there was complete drainage and added 30 mL of distilled water plus 1 mL of dye solution (3.35 g acid fuchsin+25 mL glacial acetic acid+75 mL water style). The roots of this solution were heated to the boiling point, leaving them for 30 seconds in boiling, and soon after the container was placed on the counter to reach room temperature. Subsequently, the dye solution was removed what remained, and the material was washed in tap water and placed in 20-30 mL of glycerin acidified with few drops of 5N HCl. The root segments were pressed between microscope slides and observed in optical microscope. The second stage juvenile that penetrated the roots were counted.

Statistical Analysis

The data were subjected to statistical procedures program SISVAR (FERREIRA, D. F. Análises estatisticas por meio do Sisvar para Windows Versão 4.0. In: REUNIÃO ANUAL DA REGIÃO BRASILEIRA DA SOCIEDADE INTERNACIONAL DE BIOMETRIA., 45, 2000, Sao Carlos: UFSCar, 2000, p. 255-258, 2000). In statistical analysis, means were compared by Tukey test at 5% probability.

Results and Discussion

From the data presented in Table 3 it appears that the penetration of second stage juveniles of *M. javanica* was affected in all treatments when compared with the control without any product. Treatment with aldicarb product to 20 kg ha-1 showed the lowest penetration. Of the different doses of NEMIX, the best was 8 kg ha$^{-1}$, which provided greater inhibition than the other tested doses.

TABLE 3

Number of second stage juveniles of *Meloidogyne javanica* penetrated and percentage of penetration in tomato roots cultivar. 'Santa Cruz Kada Gigante', 3 weeks after inoculation. Uberlândia, UFU, 2007.

| Products | Penetrated | Penetration % | % Inhibition of Penetration |
|---|---|---|---|
| Aldicarbe (TEMIK 150 G ® 20 kg · ha$^{-1}$) | 10.20* a** | 0.26***a | 88.00 |
| *Bacillus* spp. (NEMIX 8 kg · ha$^{-1}$) | 28.80 b | 0.72b | 66.12 |
| *Bacillus* spp. (NEMIX 6 kg · ha$^{-1}$) | 50.40 c | 1.26c | 40.70 |
| *Bacillus* spp. (NEMIX 4 kg · ha$^{-1}$) | 62.20 d | 1.57d | 26.82 |
| Control (without product application) | 85.00 e | 2.13e | — |

C.V (%) = 12.5
*Average of five repetitions
**Means followed by same letter at the column do not differ from each other by Tukey test at 5% probability
***% Penetration = N° of J$_2$/4.000 eggs It was found that the percentage of penetration of nematodes ranged from 0.26 for the dose of aldicarb and 2.13 for the control without product application.

Regarding the biological product, this may have acted in the orientation of second stage juveniles of *M. javanica* causing dispersal of juveniles, hindering the penetration thereof, or such a reduction may have been caused by interference in the process of emergence of juveniles of *M. javanica*. There is still the possibility that compounds absorbed by the egg inactivate nematode or cause deformation during development that prevent hatch.

Among the three doses evaluated the biological product based on *Bacillus* spp., the dose of 8 kg ha-1 showed better results in reducing the penetration of second stage juveniles of *M. javanica* in roots of tomato cultivar 'Santa Cruz Kada Gigante' with penetration of 0.72 percent.

Test 3

Objective: To evaluate the penetration of *Melodogyne exigua* in the tomato roots exposed to different doses of biological product based on *Bacillus* spp. under greenhouse conditions.

Obtaining the Inoculum

Getting the inoculum was made from the sample processing of coffee roots infected by *M. exigua*. The samples were taken to the Agricultural Nematology Laboratory of Institute of Agricultural Sciences and for processing, the roots were chopped into fragments of 2 cm and placed in a household blender cup containing sodium hypochlorite solution (1 part bleach: 4 parts water).

There has been grinding in the lower spin for 20 seconds. After this period, the suspension passed through a set of sieves of 200 and 500 mesh, respectively, overlap. The residue from the sieve of 500 mesh was collected, with the aid of a squeeze with water to a becker (BONETI, J. I. S.; FERRAZ, S. Modificação de metodo de Hussey e Barker para extração de ovos de *Meloidogyne exigua* de raizes de cafeeiro. Fitopatologia Brasileira, Brasilia, DF, v.6, n.3, 553p., 1981). The suspension obtained was calibrated to contain 800 nematode eggs/mL.

Installation and Driving Test

The experimental design was completely randomized design with five treatments and five replications. The genotype of tomato used was the 'Santa Cruz Kada Gigante', with the doses used the product based on *Bacillus* (NEMIX®) were 4, 6 and 8 kg ha-1, Aldibarbe nematicide (Temik® 150 G) at a dose of 20 kg of commercial product per hectare as a standard check and control tomato plants without any product to the standard penetration.

The seeds of tomato cultivar 'Santa Cruz Kada Gigante' were sown in styrofoam trays of 128 cells and after 8 days, seedlings were transplanted into plastic cups with 500 mL capacity filled with substratum Plantmax®. For inoculation, three holes were opened with 2 cm deep and spaced 2 cm from the stem of the seedling. In these three holes were distributed 5 ml suspension calibrated inoculum (4000 nematode/plastic cup). Soon after, the doses of the product based on *Bacillus* spp. were added in plastic cups with a squeeze. The nematicide aldicarb was also added immediately after inoculation, open groove around each seedling.

Evaluation of the Penetration of Juvenile Second Stage of *M. exigua* in Roots

The evaluation was done after 3 weeks of inoculation, where the roots after cutting the shoots and the separation of soil, were prepared for staining nematodes in plant tissues (Byrd Jr., et. al., An improved technique for clearing and staining plant tissues for detection of nematodes. Journal of Nematology, Lakeland, v. 5, n. 1, p. 142-143, 1983). The roots were fractured into pieces 1-2 cm and transferred to a cup Becker containing 50 mL of water to which were added 20 mL of commercial bleach (5.25% NaOCl), which resulted in a final concentration of 1.5% NaOCl. The root segments remained for 6 min in this solution, promoting a manual shaking for 10 s at intervals of 1 min. The roots were washed under running water for 30 to 45 s are kept at rest for 15 s in water to remove residual sodium hypochlorite.

Then, there was complete drainage and added 30 mL of distilled water plus 1 mL of dye solution (3.35 g acid fuchsin+25 mL glacial acetic acid+75 mL water style). The roots of this solution were heated to the boiling point, leaving them for 30 seconds in boiling, and soon after the container was placed on the counter to reach room temperature. Subsequently, we removed the dye is left, and the material was washed in tap water and placed in 20-30 mL of glycerin acidified with few drops of 5N HCl. The root segments were pressed between microscope slides that were observed in the optical microscope. We observed the root fragments and determined the number of juvenile second stage that penetrated the roots of tomato.

Maximum and Minimum Temperatures of Air Inside the Greenhouse

The daily maximum and minimum temperatures of air inside the greenhouse were recorded for the purposes of the calculation of averages for the period of the experiment.

The average maximum and minimum temperatures of air were 35.9° C. and 15.3° C., respectively.

Statistical Analysis

The data were subjected to statistical procedures program SISVAR (FERREIRA, D. F. Análises estatísticas por meio do Sisvar para Windows Versão 4.0. In: REUNIÃO ANUAL DA REGIÃO BRASILEIRA DA SOCIEDADE INTERNACIONAL DE BIOMETRIA., 45, 2000, São Carlos. Anais. São Carlos: UFSCar, 2000, p. 255-258, 2000), verifying the homogeneity of variance and normality of errors. In statistical analysis, means were compared by Tukey test at 5% probability level.

Results and Discussion

From the data presented in Table 4 and illustrated in FIG. 3, it appears that the penetration of second stage juveniles of *M. exigua* was significantly affected in all treatments when compared with the control without any product. Treatment with the aldicarb product (TEMIK) to 20 kg ha-1 was the most affected penetration. Among doses of the NEMIX product, the best was 8 kg ha$^{-1}$, which showed higher percentage of inhibition 54.13% compared to the nematicide aldicarb which showed a significant inhibition of 81.95%.

TABLE 4

Number of second stage juveniles of *Meloidogyne exigua* penetrated, the penetration percentage and percentage of inhibition in roots of tomato. 'Santa Cruz Kada Gigante', three weeks after inoculation. Uberlândia, UFU, 2007.

| Products | N° of J$_2$ of *M. exigua* penetrated | Percentage Penetration | Inhibition of penetration |
|---|---|---|---|
| Aldicarbe (TEMIK ® 150 G 20 kg · ha$^{-1}$) | 19.40* a** | 0.48*** | 81.95*** |
| Bacillus spp. (NEMIX 8 kg · ha$^{-1}$) | 49-00 b | 1.22 | 54.13 |
| Bacillus spp. (NEMIX 6 kg · ha$^{-1}$) | 66.20 c | 1.65 | 37.97 |
| Bacillus spp. (NEMIX 4 kg · ha$^{-1}$) | 81.00 c | 2.02 | 24.06 |
| Control (without application) | 106.60 d | 2.66 | — |

C.V (%) 13.04
*Average of five repetitions
**Means followed by same letter at the column do not differ from each other by Tukey test at 5% probability
***% Penetration = N° of J$_2$/4.000 eggs
***Values compared with the initial population of 4000 eggs of *M. exigua*

It is also observed that there was no difference in effect between doses of 4 and 6 kg ha-1 of the NEMIX product with percentages of penetration of 1.65 and 2.02% respectively. The percentage of penetration of nematodes ranged between 0.48 and 2.66% in control and penetration control pattern, respectively, for the initial population.

The effect of pesticides on the migration of *M. exigua* shows that there is interference in the direction causing the dispersal of juveniles. The reduction in the presence of juveniles penetrated the roots of tomato in relation to control, may also have been due to interference in the processes of hatching and orientation of juvenile *M. exigua*.

The hypothesis of reduction in nematode penetration in roots can be clarified as the ability of the bacterium, which comprises the product, to engage or connect to the surface lectins, which in this case may be minimal due to gram-positive bacteria.

The temperatures inside the greenhouse may also influence the penetration of juveniles in the roots. Some authors report that the antagonist action of some microorganisms on populations of *Meloidogyne* spp. is greater at temperatures ranging 23-25° C. than 18-32° C. (AL-HAZMI, A. S.; SCHIMITT, D. P.; SASSER, J. N. The effect of *Arthrobotrys conoides* on *Meloidogyne incognita* populations densities in corn as influenced by temperature, fungus inoculum density and of fungus introduction in the soil. Journal of Nematology, DeLeon Springs, v. 14, n. 2, p. 168-174, April, 1982).

Among the three tested doses of the product based on *Bacillus* spp., the dose of 8 kg ha-1 proved more effective in reducing the penetration of second stage juveniles of *M. exigua* in roots of tomato cultivar 'Santa Cruz Kada Gigante' with the percentage of penetration of 1.22 and 54.13% inhibition.

IN CONCLUSION

The specific combination of a *Bacillus subtilis* strain with a *Bacillus licheniformis* strains such as e.g. *Bacillus subtilis* (DSM 17231) and *Bacillus licheniformis* (DSM 17236) proves to be a strong alternative to chemical nematocidal products and also an improved composition as compared to available biological products. The combined effect of the two strains are beneficial for inhibition of the nematodes causing crop losses.

DEPOSITS AND EXPERT SOLUTION

The applicant requests that a sample of the deposited microorganisms stated below may only be made available to an expert, until the date on which the patent is granted.

The *Bacillus subtilis* strain was deposited 2005-04-07 at Deutsche Sammlung von Mikroorganismen und Zellkulturen GmbH, Mascheroder Weg 1 b, D-38124 Braunschweig (DSMZ) and given the accession No.: DSM 17231.

The *Bacillus licheniformis* strain was deposited 2005-04-07 at Deutsche Sammlung von Mikroorganismen und Zellkulturen GmbH, Mascheroder Weg 1 b, D-38124 Braunschweig (DSMZ) and given the accession No.: DSM 17236.

The deposits were made according to the Budapest treaty on the international recognition of the deposit of microorganisms for the purposes of patent procedure.

REFERENCES

EP 0705807
BR PI 0604602-9
Siddiqui and Mahmood (1999). Bioresource Technology 69; 167-179.

The invention claimed is:

1. A process for preparing a composition comprising (i) about 2.4% to about 3.0% by weight of *Bacillus subtilis* strain DSM 17231; (ii) about 2.4% to about 3.0% by weight of *Bacillus licheniformis* strain DSM 17236; (iii) about 93.0% to about 94.2% by weight maltodextrin; and (iv) about 1.0% by weight silicon dioxide, comprising mixing the *Bacillus subtilis* and the *Bacillus licheniformis* with agrochemically acceptable carriers, vehicles and/or adjuvants.

2. A method for controlling, combatting and/or conferring specific resistance to a phytonematode, comprising applying to a plant a composition comprising (i) about 2.4% to about 3.0% by weight of *Bacillus subtilis* strain DSM 17231; (ii) about 2.4% to about 3.0% by weight of *Bacillus licheniformis* strain DSM 17236; (iii) about 93.0% to about 94.2% by weight maltodextrin; and (iv) about 1.0% by weight silicon dioxide.

3. The method of claim 2, wherein the phytonematode is selected from the group consisting of *Meloidogyne, Pratylenchus, Heterodera, Globodera, Ditylenchus, Tylenchulus, Xiphinema, Radopholus, Rotylenchulus, Helicotylenchus* and *Belonolaimus*.

4. The method of claim 3, wherein the phytonematode is selected from the group consisting of *Meloidogyne incognita, Meloidogyne javanica, Meloidogyne exigua, Meloidogyne paranaensis, Heterordera glycines* and *Pratylenchus zeae*.

5. The method of claim 2, wherein the plant is selected from the group consisting of sugar cane, soybean, potato, carrot, coffee and banana.

6. The method of claim 2, comprising watering the plant with a suspension that comprises the composition.

7. The method of claim 6, comprising immersing a seedling root system in said suspension.

8. A method for controlling, combatting and/or conferring specific resistance to a phytonematode, comprising applying to a plant seed a composition comprising (i) about 2.4% to about 3.0% by weight of *Bacillus subtilis* strain DSM 17231; (ii) about 2.4% to about 3.0% by weight of a *Bacillus licheniformis* strain DSM 17236; (iii) about 93.0% to about 94.2% by weight maltodextrin; and (iv) about 1.0% by weight silicon dioxide.

9. The method of claim 8, comprising dipping the plant seed into a suspension that comprises the composition.

10. The method of claim 9, comprising applying said suspension with pelleting of said seed in alginate.

11. A method for controlling, combatting and/or conferring specific resistance to a phytonematode, comprising applying to plant soil a composition comprising (i) about 2.4% to about 3.0% by weight of *Bacillus subtilis* strain DSM 17231; (ii) about 2.4% to about 3.0% by weight of *Bacillus licheniformis* strain DSM 17236; (iii) about 93.0% to about 94.2% by weight maltodextrin; and (iv) about 1.0% by weight silicon dioxide.

\* \* \* \* \*